United States Patent
Kuechler et al.

(10) Patent No.: US 10,294,178 B2
(45) Date of Patent: May 21, 2019

(54) PROCESS FOR MAKING CYCLOHEXANONE AND/OR PHENOL

(71) Applicant: ExxonMobil Chemical Patents Inc., Baytown, TX (US)

(72) Inventors: Keith H. Kuechler, Friendswood, TX (US); Jörg F. W. Weber, Houston, TX (US); Ashley J. Poucher, Houston, TX (US); Jason D. Davis, Zachary, LA (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/551,839

(22) PCT Filed: Jan. 15, 2016

(86) PCT No.: PCT/US2016/013691
§ 371 (c)(1),
(2) Date: Aug. 17, 2017

(87) PCT Pub. No.: WO2016/160092
PCT Pub. Date: Oct. 6, 2016

(65) Prior Publication Data
US 2018/0065903 A1    Mar. 8, 2018

Related U.S. Application Data

(60) Provisional application No. 62/140,670, filed on Mar. 31, 2015.

(30) Foreign Application Priority Data

Jun. 11, 2015  (EP) .................................. 151715760

(51) Int. Cl.
C07C 7/08 (2006.01)
C07C 7/04 (2006.01)
(Continued)

(52) U.S. Cl.
CPC ................. *C07C 7/08* (2013.01); *C07C 7/04* (2013.01); *C07C 7/12* (2013.01); *C07C 37/80* (2013.01);
(Continued)

(58) Field of Classification Search
CPC .. C07C 7/08; C07C 7/12; C07C 37/80; C07C 37/82; C07C 45/79; C07C 45/83; C07C 39/04
See application file for complete search history.

(56) References Cited

U.S. PATENT DOCUMENTS

| 6,037,513 A | 3/2000 | Chang et al. |
| 9,278,897 B2 | 3/2016 | Kuechler et al. |
| 2013/0217922 A1 | 8/2013 | Kuechler et al. |

FOREIGN PATENT DOCUMENTS

| WO | 2009/025939 A | 2/2009 |
| WO | 2009/058527 A | 5/2009 |

(Continued)

OTHER PUBLICATIONS

Schmidt, Robert J., "Industrial Catalytic Processes—Phenol Production", Applied Catalysis A: General 280, 2005, pp. 89-103.

*Primary Examiner* — Brian A McCaig
(74) *Attorney, Agent, or Firm* — Kevin M. Faulkner

(57) ABSTRACT

In a process for separating a mixture comprising cyclohexanone and phenol, a solid-phase basic material, such as basic ion-exchange resin, is used to remove acid and/or sulfur from the mixture prior to separation. The process results in reduced amount of contamination such as cyclic ethers in the cyclohexanone and/or phenol products.

22 Claims, 4 Drawing Sheets

(51) Int. Cl.
*C07C 7/12* (2006.01)
*C07C 37/80* (2006.01)
*C07C 37/82* (2006.01)
*C07C 39/04* (2006.01)
*C07C 45/79* (2006.01)
*C07C 45/82* (2006.01)
*C07C 45/83* (2006.01)
*C07C 49/403* (2006.01)

(52) U.S. Cl.
CPC .............. *C07C 37/82* (2013.01); *C07C 39/04* (2013.01); *C07C 45/79* (2013.01); *C07C 45/82* (2013.01); *C07C 45/83* (2013.01); *C07C 49/403* (2013.01); *C07C 2601/14* (2017.05)

(56) References Cited

FOREIGN PATENT DOCUMENTS

| WO | 2009/058531 A | 5/2009 | |
|----|---------------|--------|--|
| WO | 2009/128984 A | 10/2009 | |
| WO | 2009/131769 A | 10/2009 | |
| WO | WO 2013/052216 A1 * | 4/2013 | ............. C07C 37/08 |
| WO | 2013/165659 A | 11/2013 | |
| WO | 2014/081597 A | 5/2014 | |
| WO | 2014/137623 A | 9/2014 | |

* cited by examiner

PROCESS FOR MAKING CYCLOHEXANONE AND/OR PHENOL

PRIORITY CLAIM TO RELATED APPLICATIONS

This application is a National Phase Application claiming priority to PCT Application Serial No. PCT/US2016/013691 filed Jan. 15, 2016, and U.S. Provisional Application No. 62/140,670, filed Mar. 31, 2015, the disclosures of which are incorporated herein by reference.

TECHNICAL FIELD

The present invention relates to processes for making cyclohexanone and/or phenol. In particular, the present invention relates to processes for making cyclohexanone and/or phenol from cyclohexylbenzene oxidation. The present invention is useful, e.g., in making cyclohexanone and/or phenol from cyclohexylbenzene produced by benzene hydrogenation.

BACKGROUND

Phenol and cyclohexanone are important compounds in the chemical industry and are useful in, for example, production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone.

Thus, a process that uses higher alkenes instead of propylene as feed and coproduces higher ketones, such as cyclohexanone, rather than acetone may be an attractive alternative route to the production of phenols. There is also a growing demand for cyclohexanone.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof, that the resultant cyclohexylbenzene can be oxidized to the corresponding hydroperoxide which can then be decomposed to produce phenol and cyclohexanone in the presence of an acid such as sulfuric acid in a cleavage step. This cyclohexylbenzene-based process for co-producing phenol and cyclohexanone can be highly efficient in making these two important industrial materials.

The effluent from the cleavage step typically contains phenol, cyclohexanone, the acid catalyst, cyclohexylbenzene, and additional contaminants that may be produced as byproducts from the oxidation and/or cleavage step. To obtain pure phenol and cyclohexanone, the cleavage effluent can be treated first by a basic material, such as an amine (e.g., pentane-1,5-diamine; hexane-1,6-diamine; hexane-1,5-diamine; 2-methylpentane-1,5-diamine; ethylene diamine; diethylene triamine; triethylene tetramine; propylene diamine; and the like), typically in liquid phase under the operation conditions, to neutralize at least a portion of the acid catalyst. The neutralized cleavage effluent can be then separated by, e.g., a distillation column. Because phenol and cyclohexanone forms an azeotrope, complete separation of phenol from cyclohexanone to obtain two pure products can be achieved only with the aid of an extractive distillation solvent. It has been found that, the presence of sulfur and/or acid in the feed into the distillation columns, including but not limited to the extractive distillation column, can significantly hamper the effective separation and/or operations of the distillation column(s), leading to the presence of unwanted contaminants in one or both of the cyclohexanone and phenol products.

Thus, there are needs for (i) a process for effectively separating a mixture comprising cyclohexanone, phenol, cyclohexylbenzene, and a sulfur-containing component to obtain high purity cyclohexanone and/or phenol, and (ii) a process for making phenol and/or cyclohexanone form an extractive distillation feed comprising phenol and cyclohexanone to obtain high purity phenol and/or cyclohexanone. The present invention satisfies these needs.

SUMMARY

It has been found, in a surprising manner, that by contacting the feed materials to the distillation columns, including but not limited to the first distillation column for separating the cleavage effluent and the extractive distillation column for separating a cyclohexanone/phenol mixture, with a solid-phase basic material before feeding them into the distillation columns, one can significantly reduce the level of contaminants present in the final phenol and/or the cyclohexanone products.

A first aspect of the present invention relates to a process for separating a first mixture comprising cyclohexanone, phenol, cyclohexylbenzene, and a sulfur-containing component, comprising the following steps: (I) contacting the first mixture with a pre-distillation solid-phase basic material to produce a second mixture comprising the sulfur-containing component at a concentration lower than in the first mixture; (II) supplying the second mixture into a first distillation column operating at a temperature of at least 120° C.; and (III) obtaining an upper effluent and a lower effluent from the first distillation column, wherein the upper effluent has a higher concentration in cyclohexanone than the lower effluent, and the lower effluent has a higher cyclohexylbenzene concentration than the upper effluent.

A second aspect of the present invention relates to a process for making phenol and/or cyclohexanone from an extraction distillation feed comprising phenol and cyclohexanone, comprising the following steps: (i) controlling the concentration of an acid in the extraction distillation feed at a level no greater than 10 ppm by weight, based on the total weight of the extraction distillation feed; (ii) supplying at least a portion of the extraction distillation feed and an extractive distillation solvent into an extractive distillation column; (iii) obtaining an upper cyclohexanone effluent and a lower extraction effluent from the extractive distillation column wherein the upper cyclohexanone effluent comprises cyclohexanone at a concentration of at least 90 wt %, and the lower extraction effluent comprises phenol and the extractive distillation solvent; (iv) supplying at least a portion of the lower extraction effluent to a solvent distillation column; and (v) obtaining an upper phenol effluent and a lower solvent effluent from the solvent distillation column.

DETAILED DESCRIPTION

Figure 1:
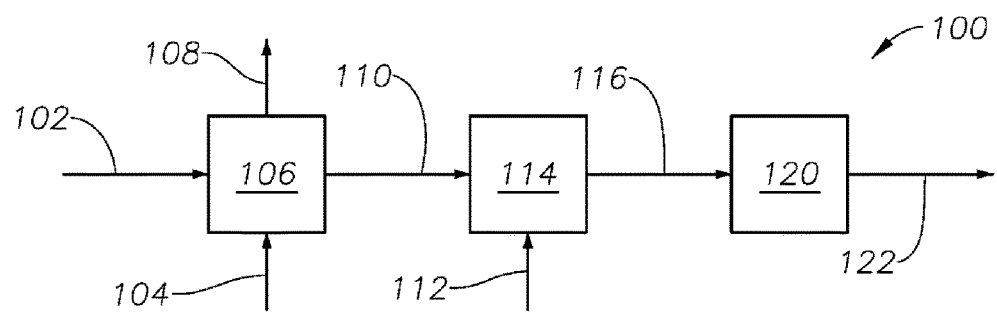
FIG. 1 is a schematic drawing showing an overall continuous process for making cyclohexanone and/or phenol from cyclohexylbenzene.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a distillation column" include embodiments where one, two or more distillation columns are used, unless specified to the contrary or the context clearly indicates that only one distillation column is used. Likewise, "a C12+ component" should be interpreted to include one, two or more C12+ components unless specified or indicated by the context to mean only one specific C12+ component.

A "complex" as used herein means a material formed by identified components via chemical bonds, hydrogen bonds, and/or physical forces.

An "operation temperature" of a distillation column means the highest temperature liquid media inside the column is exposed to during normal operation. Thus, the operation temperature of a column is typically the temperature of the liquid media in the reboiler, if the column is equipped with a reboiler.

In the present application, sulfur concentration in a material is expressed in terms of proportion (ppm, weight percentages, and the like) of the weight of elemental sulfur relative to the total weight of the material, even though the sulfur may be present in various valencies other than zero. Sulfuric acid concentration is expressed in terms of proportion (ppm, weight percentages, and the like) of the weight of $H_2SO_4$ relative to the total weight of the material, even though the sulfuric acid may be present in the material in forms other than $H_2SO_4$. Thus, the sulfuric acid concentration is the total concentration of $H_2SO_4$, $HSO_4^-$, $R—HSO_4$, and $SO_3$ in the material.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

In the present disclosure, a location "in the vicinity of" an end (top or bottom) of a column means a location within a distance of a*Hc from the end (top or bottom) of the column, where Hc is the height of the column from the bottom to the top, and a1≤a≤a2, where a1 and a2 can be, independently: 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, as long as a1<a2. For example, a location in the vicinity of an end of a column can have an absolute distance from the end (top or bottom) of at most D meters, where D can be 5.0, 4.5, 4.0, 3.5, 3.0, 2.5, 2.0, 1.5, 1.0, 0.8, 0.5, 0.4, 0.3, 0.2, 0.1, or 0.

An "upper effluent" as used herein may be at the very top or the side of a vessel such as a distillation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent. The "same level" on a distillation column means a continuous segment of the column with a total height no more than 5% of the total height of the column.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a distillation column.

As used herein, the generic term "dicyclohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, dicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

The term "MCM-22 type material" (or "material of the MCM-22 type" or "molecular sieve of the MCM-22 type" or "MCM-22 type zeolite"), as used herein, includes one or more of: (i) molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference; (ii) molecular sieves made from a common second degree building block, being a 2-dimensional tiling of such MWW framework topology unit cells, forming a monolayer of one unit cell thickness, desirably one c-unit cell thickness; (iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve used in the catalyst of the present disclosure is selected from (a) MCM-49; (b) MCM-56; and (c) isotypes of MCM-49 and MCM-56, such as ITQ-2.

The process and systems for making cyclohexanone disclosed herein can be advantageously used for making cyclohexanone and/or phenol from any feed mixture comprising phenol, cyclohexanone and cyclohexylbenzene. While the feed may be derived from any process or source, it is preferably obtained from the acid cleavage of a mixture comprising cyclohexylbenzene hydroperoxide and cyclohexylbenzene, which, in turn, is preferably obtained from aerobic oxidation of cyclohexylbenzene, which, in turn, is preferably obtained from benzene. Steps of these preferred processes are described in detail below.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

(Reaction-2)

Side reactions may occur in Reaction-1 and Reaction-2 to produce some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step. Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Details of feed materials, catalyst used, reaction conditions, and reaction product properties of benzene hydroalkylation, and transalkylation and dealkylation can be found in, e.g., the following copending, co-assigned patent applications: U.S. Provisional Patent Application Ser. No. 61/972,877, entitled "Process for Making Cyclohexylbenzene and/or Phenol and/or Cyclohexanone," and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

(Reaction-3)

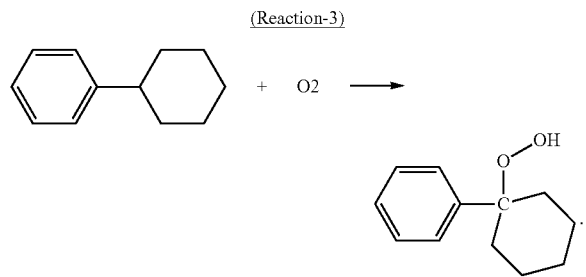

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

In exemplary processes, the oxidation step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor to effect the oxidation of cyclohexylbenzene.

The oxidation may be conducted in the absence or presence of a catalyst, such as a cyclic imide type catalyst (e.g., N-hydroxyphthalimide).

Details of the feed material, reaction conditions, reactors used, catalyst used, product mixture composition and treatment, and the like, of the oxidation step can be found in, e.g., the following copending, co-assigned patent applications: U.S. Provisional Patent Application Ser. No. 61/972,877, entitled "Process for Making Cyclohexylbenzene and/or Phenol and/or Cyclohexanone," and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

(Reaction-4).

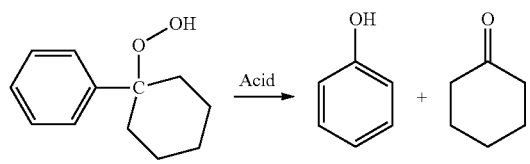

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Feed composition, reaction conditions, catalyst used, product mixture composition and treatment thereof, and the like, of this cleavage step can be found in, e.g., the following copending, co-assigned patent applications: U.S. Provisional Patent Application Ser. No. 61/972,877, entitled "Process for Making Cyclohexylbenzene and/or Phenol and/or Cyclohexanone," and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Separation and Purification

The cleavage product mixture exiting the cleavage reactor typically comprises phenol, cyclohexanone, cyclohexylbenzene, the acid catalyst, and additional contaminants that may be byproduct from the oxidation and/or the cleavage steps. Before separation of the cleavage product mixture to obtain the desired phenol and/or cyclohexanone product(s), at least a portion of it may be subjected to a neutralization reaction. Where a liquid acid such as sulfuric acid is used as the cleavage catalyst, at least a portion of the cleavage reaction product can be neutralized by one or more basic materials, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid and undesirable side reactions that may occur in the separation step. Desirably, the thus formed amine sulfate salt has a boiling point higher than that of cyclohexylbenzene.

A portion of the neutralized cleavage reaction product can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidation step. Since the cyclohexylbenzene separated from the cleavage product mixture may contain phenol and/or olefins such as cyclohexenylbenzenes, the material may be subjected to treatment with an aqueous composition comprising a base and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower fraction comprising primarily phenol, and some cyclohexanone. Cyclohexanone cannot be completely separated from phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., sulfolane, and glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Where an acid, such as sulfuric acid, is used as the catalyst in the cleavage step, and a liquid amine is used as the neutralizing agent to neutralize at least a portion of the acid before the cleavage product mixture is fed into the first distillation column, the acid will react with the amine to form a complex that is fed into the first distillation column as well. It had been hoped that given the high boiling point of the complex, it would stay in the bottom fraction of the first distillation column, and therefore all sulfur would be removed completely from the bottoms of the first distillation column. However, in a very surprising manner, it has been found that sulfur was present in the upper fraction comprising cyclohexanone, phenol exiting the first distillation column.

Without intending to be bound by a particular theory, it is believed that the complex between the acid catalyst and the organic amine, if present in the feed to the first distillation column, can decompose at least partially in the first distillation column, due to the high operating temperature therein (i.e., the highest temperature the liquid media is exposed to in the first distillation column, typically in the vicinity of the bottom of the column) of at least 120° C. (even 130° C., 140° C., 150° C., 160° C., 170° C., 180° C., 190° C., 200° C., 210° C., 220° C., 230° C., 240° C., or even 250° C.) is used, necessitated by the separation of cyclohexylbenzene present therein at high concentrations (e.g., at least 5 wt %, or 10 wt %, or 15 wt %, or 20 wt %, or 25 wt %, or 30 wt %, or 35 wt %, or 40 wt %, or 45 wt %, or even 50 wt %, based on the total weight of the cleavage product mixture), which has a very high normal boiling temperature (240° C., compared to the normal boiling temperature of cumene of 152° C.). The decomposition of the complex likely produces, among others, $SO_3$, which can easily travel upwards along the first distillation column to upper locations, where it can recombine at least partially with water to form $H_2SO_4$. This operation temperature can be significantly higher than the distillation temperature the mixture of cumene, phenol, and acetone is exposed to in the first distillation column in the cumene process for making phenol and acetone.

Thus, the presence of acid, especially strong acid such as $SO_3$ and/or sulfuric acid in the first distillation column, can catalyze many undesirable side reactions between and among the many components present in the distillation mixture, leading to the formation of byproducts and/or premature malfunction of the distillation column. Furthermore, at high operation temperature, prolonged exposure to the acid can cause significant corrosion to the column equipment. The acid species can also make their way into the various fractions drawn from the different locations of the first distillation column, causing different problems in subsequent steps where the fractions are further processed.

Therefore, treating the cleavage product mixture before it enters into the first distillation column using a solid-phase basic material according to the present invention is highly advantageous and desirable. Doing so would reduce or eliminate the presence of acid species in media inside the first distillation column, avoid undesirable side reactions and byproducts formed as a result of contact with the acid species, reduce corrosion of the first distillation column caused by the acid species and the associated repair and premature replacement, and prevent undesirable side reactions and byproduct formation in subsequent steps.

Such basic materials useful for the present invention, advantageously in solid-phase under the operation conditions, can be selected from (i) oxides of alkali metals, alkaline earth metals, and zinc; (ii) hydroxides of alkali metals, alkaline earth metals, and zinc; (iii) carbonates of alkali metals, alkaline earth metals, and zinc; (iv) bicarbonates of alkali metals, alkaline earth metals, and zinc; (v) complexes of two or more of (i), (ii), (iii), and (iv); (vi) solid amines; (vii) ion-exchange resins; and (viii) mixtures and combinations of two or more of (i), (ii), (iii), (iv), (v), (vi), and (vii). Oxides, hydroxides, carbonates and bicarbonates of alkali, alkaline earth metals, and zinc can react with acid to form salts thereof, which preferably are also in solid-phase under the operation conditions. Preferably, an ion exchange resin is used. Such ion exchange resin preferably comprise groups on the surface thereof capable of adsorbing and/or binding with protons, $SO_3$, $HSO_4^-$, $H_2SO_4$, complexes of sulfuric acid, and the like. The ion exchange resin can comprise a strong and/or a weak base resin. Weak base resins primarily function as acid adsorbers. These resins are capable of sorbing strong acids with a high capacity. Strong base anion resins can be quarternized amine-based products capable of sorbing both strong and weak acids. Commercial examples of basic ion exchange resins useful in the present invention include but are not limited to: Amberlyst® A21 basic ion exchange resin available from Dow Chemical Company.

Desirably, as a result of the treatment of the cleavage product mixture using the present invention, substantially all sulfur and/or acid is removed from the cleavage product mixture before being fed into the first distillation column. Thus, the feed supplied to the first distillation column may exhibit one or more of the following traits (i), (ii), (iii), (iv), and (v):

(i) total acid concentration, based on the total weight of the mixture fed into the first distillation column, of at most 50 ppm, such as no higher than 40 ppm, 30 ppm, 20 ppm, 10 ppm, 8 ppm, 6 ppm, 5 ppm, 4 ppm, 3 ppm, 2 ppm, or even 1 ppm;

(ii) total sulfuric acid concentration, based on the total weight of the mixture fed into the first distillation column, of at most 50 ppm, such as no higher than 40 ppm, 30 ppm, 20 ppm, 10 ppm, 8 ppm, 6 ppm, 5 ppm, 4 ppm, 3 ppm, 2 ppm, or even 1 ppm;

(iii) total sulfur concentration, based on the total weight of the mixture fed into the first distillation column, of at most 50 ppm, such as no higher than 40 ppm, 30 ppm, 20 ppm, 10 ppm, 8 ppm, 6 ppm, 5 ppm, 4 ppm, 3 ppm, 2 ppm, or even 1 ppm;

(iv) total acid concentration in the feed supplied to the first distillation column is at most 10%, or 9%, 8%, 7%, 6%, 5%, 4%, 3%, 2%, or even 1%, of the total acid concentration in the cleavage product mixture prior to being treated by using the method of the present invention; and (v) total sulfur concentration in the feed supplied to the first distillation column is at most 10%, or 9%, 8%, 7%, 6%, 5%, 4%, 3%, 2%, or even 1%, of the total sulfur concentration in the cleavage product mixture prior to being treated by using the method of the present invention.

Cleavage of cyclohexylbenzene hydroperoxide in a media comprising cyclohexylbenzene hydroperoxide, cyclohexanone, phenol, and cyclohexylbenzene typically uses acid catalyst, such as sulfuric acid, at concentrations higher than in the cleavage of cumene hydroperoxide in a media comprising cumene hydroperoxide, phenol, acetone, and cumene. Thus, in cyclohexylbenzene hydroperoxide cleavage, sulfuric acid concentration in the media can range from, e.g., 50 (or 60, 80, 100, 150, 200, 250, 300, 350, 400, 450, 500) ppm to 2000 (or 1800, 1600, 1500, 1400, 1200, 1000, 800, 600) ppm, based on the total weight of the cleavage reaction media. If an organic amine is used to neutralize the acid in the cyclohexylbenzene hydroperoxide cleavage product mixture, a large quantity of the amine would be consumed, which would represent quite substantial costs to the overall process. In the present invention, either inexpensive solid-phase bases such as hydroxides, carbonates and bicarbonates (e.g., NaOH, KOH, $Na_2CO_3$, $NaHCO_3$, $CaCO_3$, and the like), or regenerable ion exchange resins, can be used, thereby reducing the overall costs to the process. Furthermore, where a large quantity of amine is used, a large quantity of amine acid complex material would be produced and delivered to the first distillation column. Even at relatively low distillation column operation temperature where only a very small percentage of the complex decomposes, because of the large quantity of the complex supplied to the first distillation column, a non-negligible quantity of $SO_3$, $HSO_4^-$, $RHSO_4$, and/or $H_2SO_4$ may nonetheless be produced and travel along the column to the various fractions drawn from the column. Therefore, using the process of the present invention to treat cleavage product mixture comprising acid at a high concentration to remove substantially all of the acid before the first distillation column is particularly advantageous.

Total sulfur concentration in the organic media can be determined by using conventional methods such as gas chromatography followed by mass spectrometry (GC-MS), liquid chromatography, ICP-AES, ICP-MS, and the like. For example, total sulfur measurement techniques may include ASTM Standard Test Method D 5504: Determination of Sulfur Compounds in Natural Gas and Gaseous Fuels by Gas Chromatography and Chemiluminescence; ASTM D 5623: Sulfur Compounds in Light Petroleum Liquids by Gas Chromography and Sulfur Selective Detection; ASTM D 7011: Determination of Trace Thiophene in Refined Benzene by Gas Chromatography and Sulfur Selective Detection; and ASTM D5453 Standard Test Method for Determination of Total Sulfur in Light Hydrocarbons, Spark Ignition Engine Fuel, Diesel Engine Fuel, and Engine Oil by Ultraviolet Fluorescence. Total sulfur measurement instruments may include those utilizing the principles of Energy Dispersive X-Ray Fluorescence, (Pulsed) Ultra Violet Fluorescence ((P)UVF), and Sulfur Chemiluminescence Detection (SCD), for example utilizing the combustion of sulfur compounds to form sulfur monoxide (SO) and the chemiluminescence reaction of SO with ozone ($O_3$), and other pyrofluorescence and pyro-chemiluminescence technologies.

Sulfuric acid concentration in the organic media can be determined by using conventional methods such as titration, gas chromatography followed by mass spectrometry (GC-MS), liquid chromatography, ICP-AES, ICP-MS, and the like. Sulfuric acid concentration may be derived from the measured total sulfur concentration, or vice versa.

Total sulfur concentration in the organic media can be determined by using conventional methods such as gas chromatography followed by mass spectrometry (GC-MS), liquid chromatography, ICP-AES, ICP-MS, and the like.

After treatment using the method of the present invention, both total acid concentration and acid precursor concentration in the feed supplied to the first distillation column can be exceedingly low. Accordingly, the first distillation column can be operated at a high operation temperature, such as temperatures higher than the disassociation temperatures of complex materials formed between the acid catalyst used in the cleavage step, such as sulfuric acid, and the following organic amines: (i) pentane-1,5-diamine; (ii) 1-methylhexane-1,5-diamine; (iii) hexane-1,6-diamine; (iv) 2-methylpentane-1,5-diamine; (v) ethylene diamine; (vi) propylene diamine; (vii) diethylene triamine; and (viii) triethylene tetramine, without the concern of issues associated with acid produced from thermal dissociation thereof under such high operation temperature.

Acid, especially strong acid such as $SO_3$, $HSO_4^-$, $RHSO_4$, and/or $H_2SO_4$, if allowed to enter the extractive distillation column, can catalyze side reactions therein, leading to the formation of undesirable contaminants. For example, where an alcohol, such as a glycol having the general formula HO—R—OH, is used as the extractive distillation solvent, inter-molecular and intra-molecular condensation reactions as follows can occur in the presence of the acid:

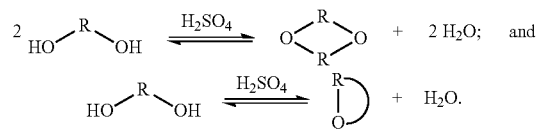

Where diethylene glycol (DEG) is used (i.e., where —R— is —$CH_2CH_2$—O—$CH_2CH_2$—) as the extractive distillation solvent, the following cyclic ether byproducts can be produced as a result of inter-molecular and intra-molecular condensation reactions:

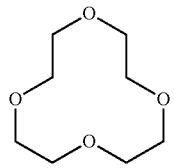

(1,4,7,10-tetraoxacyclododecane), and

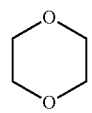

(1,4-dioxane).

Where ethylene glycol is used (i.e., where —R— is —$CH_2CH_2$—) as the extractive distillation solvent, in whole or in part, 1,4,7,10-tetraoxacyclododecane, 1,4-dioxane, ethylene epoxide, and

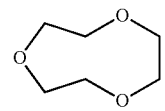

(1,4,7-trioxonane) may be produced as a result of intermolecular and intra-molecular condensation reactions.

Where a mixture of DEG and ethylene glycol is used as the extractive distillation solvent, 1,4,7,10-tetraoxacyclododecane, 1,4,7-trioxonane, 1,4-dioxane, and ethylene epoxide may be produced as a result of inter-molecular and intramolecular condensation reactions.

Light weight cyclic ethers such as 1,4-dioxane can become contaminants both in the cyclohexanone product and the phenol product. While these cyclic ethers such as 1,4-dioxane can be separated from cyclohexanone using a conventional distillation column, it would be highly preferable if they are not produced in the first place, whereby eliminating the costs of an additional distillation column and its operation. On the other hand, it has been found to be extremely difficult to separate 1,4-dioxane from phenol using conventional distillation. Therefore, it would be highly desirable that cyclic ether byproducts do not form in the extractive distillation column.

Accordingly, it would be highly desirable that acid capable of catalyzing alcohol condensation is introduced into the extractive distillation column from the extractive distillation feed and solvent used at a very low concentration, preferably at a non-detectable level. It has been found that the concentration of sulfur in the extractive distillation column correlates to acid concentration capable of catalyzing the condensation reactions. This is particularly true where sulfuric acid is used as the cleavage catalyst. Accordingly, it is highly desirable that the total concentration of sulfur in the extractive distillation feed and solvent is very low, preferably at a non-detectable level.

Thus, in the present invention, methods are proposed to control the acid and/or sulfur concentration in the extractive distillation feed. Desirably, acid concentration in the extractive distillation feed is controlled at a level of at most 50 ppm, such as no higher than 40 ppm, 30 ppm, 20 ppm, 10 ppm, 8 ppm, 6 ppm, 5 ppm, 4 ppm, 3 ppm, 2 ppm, or even 1 ppm, based on the total weight of the extractive distillation feed comprising phenol and cyclohexanone. Desirably, acid concentration in the extractive distillation solvent fed to the extractive distillation column is controlled at a level of at most 50 ppm, such as no higher than 40 ppm, 30 ppm, 20 ppm, 10 ppm, 8 ppm, 6 ppm, 5 ppm, 4 ppm, 3 ppm, 2 ppm, or even 1 ppm, based on the total weight of the extractive distillation solvent.

One method to control the acid concentration in the extractive distillation feed at such low level is by contacting it with a basic material, preferably a solid basic material, before the feed is supplied into the extractive distillation column. Such basic material advantageously is in solid-phase under the operation conditions, and can be the same or different material useful for treating the cleavage product mixture for removing acid therefrom before the first distillation column as described above.

In one example, controlling acid concentration in the extractive distillation feed can be effected, in whole or in part, immediately before the extractive distillation column by contacting the feed with a basic, solid-phase material. Thus, after treatment, the extractive distillation feed is supplied immediately into the extractive distillation column without passing through an intervening distillation column. In this case, neutralization of at least a majority of the acid in the cleavage product mixture before the first distillation column is still desired due to the detrimental effect the acid may have on the first distillation column and the distillation process therein. However, neutralization before the first distillation column can be effected by using the same basic material used immediately before the extractive distillation column, or a different one, for example, a liquid organic amine.

Alternatively, controlling acid concentration in the extractive distillation feed can be effected at one or more locations upstream to a vessel such as a distillation column that is upstream to the extractive distillation. Preferably, such controlling step is effected before the first distillation column after the cleavage reactor as described above.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

DESCRIPTION ACCORDING TO THE DRAWINGS

FIG. 1

In FIG. 1, an exemplary process for making cyclohexanone and phenol from cyclohexylbenzene, 100, is schematically illustrated. Preferably the method is continuous, with streams continuously added to and removed from the equipment items in a controlled fashion to maintain desired equipment inventory and operating conditions within the equipment and lines. It is to be understood that batch operations with intermittent introduction and removal of streams, or semi-batch operations where some streams are intermittently introduced and removed and some are continuously removed are also well within present invention scope. In such semi-batch operations, a continuous stream comprising oxygen, discussed below, is particularly preferable.

The feedstock in line 102, comprising cyclohexylbenzene, is provided to oxidation reactor 106. A stream comprising oxygen in line 104, conveniently air, is also provided to oxidation reactor 106. The stream comprising oxygen in line 104 may also be one derived from air, for example, air that has been compressed and filtered to remove particulates, air that has been compressed and cooled to condense and remove water, or a stream that has been enriched in oxygen above the natural approximately 21 mol % in air through membrane enrichment of air, cryogenic separation of air or other means within the ken of the skilled artisan.

Oxidation reactor 106 may be any type of reactor known to those skilled in the art, for example, comprising a simple, largely open vessel container with a distributor inlet for the stream comprising oxygen in line 104, or otherwise ensure good contacting of oxygen and cyclohexylbenzene hydroperoxide. Oxidation reactor 106 may have means to withdraw and pump a portion of the contents through a suitable cooling device and return the cooled portion to oxidation reactor 106, thereby managing the exothermicity of the oxidation reaction. Alternatively, cooling coils providing indirect cooling, say by cooling water, may be operated within oxidation reactor 106 to remove the generated heat. In other embodiments, oxidation reactor 106 comprises a plurality of such oxidation reactors in series, each conducting a portion of the conversion reaction, optionally operating at different conditions selected to enhance the oxidation reaction at the pertinent conversion range in each.

Conditions within oxidation reactor 106 are such that an oxidation reaction takes place, causing cyclohexylbenzene hydroperoxide to form. Conveniently conditions are selected to favor the formation of cyclohexyl-1-phenyl-1-hydroperoxide well above other hydroperoxides and dihydroperoxides. In one particular embodiment, N-hydroxyphthalimide (NHPI) is also introduced to oxidation reactor 106, by means not shown in FIG. 1, to enhance selectivity to cyclohexyl-1-phenyl-1-hydroperoxide.

As the oxidation reaction continues, oxygen is depleted and an oxygen depleted stream in line 108 is removed from oxidation reactor 106. When the stream comprising oxygen in line 104 is air, the oxygen depleted stream in line 108 is typically enriched in nitrogen. When the oxidation reaction is conducted at or near atmospheric pressure, the oxygen depleted stream in line 108 may also contain lower volatility byproducts of the oxidation reaction, such as water, along with minor amounts of cyclohexylbenzene, among other components that may be vapor under the conditions in oxidation reactor 106. In an operation not shown in FIG. 1, the oxygen depleted stream in line 108 may be further processed to recover the cyclohexylbenzene, remove water, and otherwise make the cyclohexylbenzene fit for recycle as feed to oxidation reactor 106, and make other streams suitable for other uses or disposal.

An oxidation reaction product including cyclohexylbenzene hydroperoxide in line 110, conveniently rich in cyclohexyl-1-phenyl-1-hydroperoxide but potentially including other hydroperoxides and dihydroperoxides, is withdrawn from oxidation reactor 106. In an embodiment where NHPI is introduced to oxidation reactor 106, the oxidation reaction product including cyclohexylbenzene hydroperoxide may contain NHPI.

The oxidation product including cyclohexylbenzene hydroperoxide in line 110, along with sulfuric acid to promote a cleavage reaction in line 112, is provided to cleavage reactor 114. In one embodiment, the material that will promote a cleavage reaction in line 112 is a mixture of sulfuric acid and water. Conditions in cleavage reactor 114 are such that a cleavage reaction takes place, causing the cyclohexylbenzene hydroperoxide, conveniently cyclohexyl-1-phenyl-1-hydroperoxide but also any other hydroperoxides and dihydroperoxide present, to decompose to materials such as phenol, cyclohexanone and a contaminant byproduct. A cleavage product including phenol, cyclohexanone, any unreacted cyclohexylbenzene, a contaminant byproduct and sulfuric acid in line 116 is withdrawn from cleavage reactor 114.

Cleavage reactor 114 may be any type of reactor known to those skilled in the art, for example, comprising a simple, largely open vessel container operating in a near Continuous Stirred Tank Reactor mode, or a simple, open length of pipe operating in a near Plug Flow Reactor mode. Cleavage reactor 114 may have means to withdraw and pump a portion of the contents through a suitable cooling device and return the cooled portion to cleavage reactor 114, thereby managing the exothermicity of the cleavage reaction, or it may be operated in an adiabatic fashion. In one embodiment, the material promoting the cleavage reaction may be introduced to cleavage reactor 114 in such a circulating portion of the contents, with or without cooling. Alternatively, cooling coils providing indirect cooling, say by cooling water, may be operated within cleavage reactor 114 to remove the generated heat. In other embodiments, cleavage reactor 114 comprises a plurality of such cleavage reactors in series, each conducting a portion of the conversion reaction, optionally operating in different modes and at different conditions selected to enhance the cleavage reaction at the pertinent conversion range in each.

The cleavage product in line 116 is directed to a solid basic medium contacting device 120. In one embodiment, the solid basic medium in contacting device 120 is a basic ion exchange resin, e.g., Amberlyst® A21 available from Dow Chemical Company. The contacting device 120 is a vessel filled with the solid in a manner conducive to fixing the sulfur on the solid basic medium as the cleavage product including sulfuric acid flows over it, and the vessel dimensions and quantity of solid are such as to provide the desired contacting residence time and flow parameters at the given conditions. Conditions within contacting device 120 are such that at least a portion of the sulfuric acid remains on the solid basic medium and is removed from the cleavage product to produce a low sulfur cleavage product stream in line 122 having less than 10 wppm sulfur and/or sulfuric acid. The solid basic medium in contacting device 120 may be used until it loses effectiveness and then regenerated or replaced in an appropriate manner. The low sulfur cleavage product stream in line 122 having less than 10 wppm sulfur and/or sulfuric acid subjected to further processing by means not shown in FIG. 1 to provide a phenol rich stream comprising no greater than 10 wppm 1,4-dioxane and a cyclohexanone rich stream comprising no greater than 10 wppm 1,4-dixoane.

FIG. 2

Figure 2:
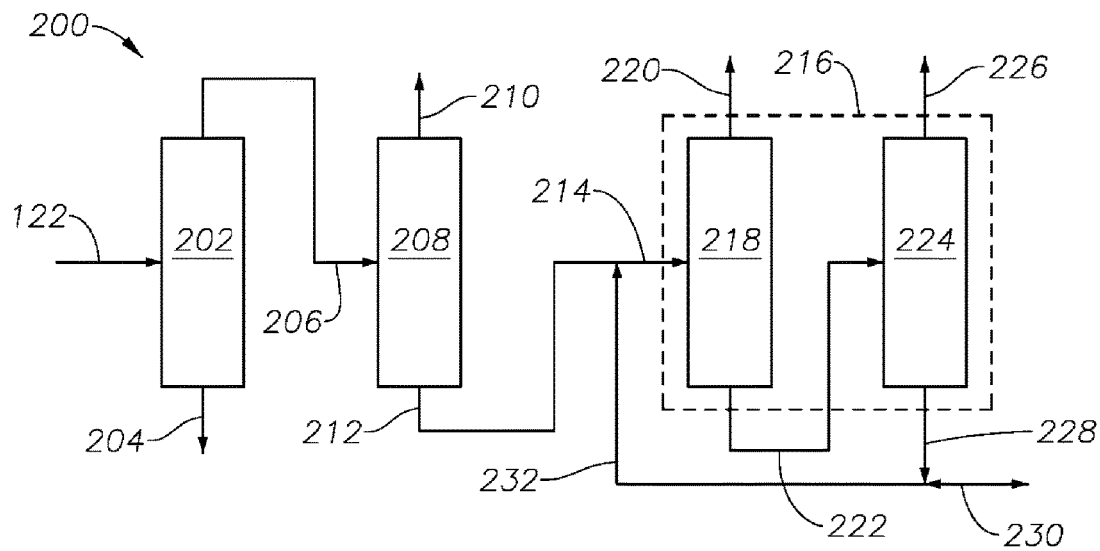
FIG. 2 is a schematic drawing showing a separation process for separating a mixture comprising cyclohexanone, cyclohexylbenzene, and phenol.

In FIG. 2, an overall process for separating cyclohexanone and phenol 200 in the method of the present invention is schematically shown. Numerous equipment and operations (not shown) may be employed in this process by one having ordinary skill in the art in the light of the description herein. Preferably the method is continuous, with streams continuously added to and removed from the equipment items in a controlled fashion to maintain desired equipment inventory and operating conditions within the equipment and lines. This description according to FIG. 2 assumes such an embodiment, but batch operations with intermittent introduction and removal of streams, or semi-batch operations where some streams are intermittently introduced and removed and some are continuously removed are also well within present invention scope.

A low sulfur cleavage product stream in line 122 having less than 10 wppm sulfur and/or sulfuric acid, produced in accordance with the description of FIG. 1 above, is provided to a first distillation column 202. First distillation column 202 serves to separate from the low sulfur cleavage product stream in line 122 a first bottoms product rich in cyclohexylbenzene and lean in phenol and components of higher volatility than phenol in line 204, and as an overhead product a first combined product stream rich in phenol and cyclohexanone and lean in cyclohexylbenzene and components of lower volatility than cyclohexylbenzene in line 206. The conditions within first distillation column 202 to which the low sulfur cleavage product stream in line 122 having less than 10 wppm sulfur and/or sulfuric acid are exposed include a temperature of at least 120° C.

The first combined product stream in line 206 further contains components of higher volatility than cyclohexanone as contaminants, e.g., hexanal, pentanoic acid and water. The first combined product stream in line 206 is to be directed to a second distillation column 208 that serves to separate as a second overhead product a stream rich in those components of lower volatility and lean in phenol and cyclohexanone in line 210, and a second combined product stream as bottoms in line 212 that is richer in phenol and cyclohexanone than the first combined product stream.

Remaining with FIG. 2, the second combined product stream in line 212 is directed to an extractive distillation system within dashed line box 216, comprising, in one embodiment, an extraction column 218, and a solvent recovery column 224. In particular, the second combined product stream in line 212 is mixed with a circulating diethylene glycol solvent stream in line 232 to form a combined mixture and solvent stream in line 214 that is provided to extractive distillation column 218. Extraction column 218 is operated under conditions to separate from the combined mixture and solvent stream in line 214 a cyclohexanone rich stream in line 220 as an overhead product that is richer in cyclohexanone than the combined mixture and solvent stream in line 214, for example, containing 99.99 wt % of the cyclohexanone and only 0.01 wt % of the phenol found in the combined mixture and solvent stream, and no detectable diethylene glycol. Further, the cyclohexanone rich stream in line 220 contains no greater than 10 wppm 1,4-dixoane.

Extraction column 218 is further operated under conditions to separate from the second combined mixture and solvent stream in line 214 a phenol and diethylene glycol rich and cyclohexanone lean stream as a bottoms product in line 222, for example, containing 99.99 wt % of the phenol, only 0.01 wt % of the cyclohexanone, and substantially all the diethylene glycol solvent found in the combined mixture and solvent stream in line 214.

The phenol and diethylene glycol rich and cyclohexanone lean stream in line 222 is provided to solvent recovery column 224. Solvent recovery column 224 is operated under conditions to separate from the phenol and diethylene glycol rich and cyclohexanone lean stream in line 222 a phenol rich stream in line 226 as an overhead product that is richer in phenol than the phenol and diethylene glycol rich and cyclohexanone lean stream in line 222, for example, containing 99.9 wt % of the phenol found in the phenol and diethylene glycol rich and cyclohexanone lean stream in line 222, and no detectable diethylene glycol. Solvent recovery column 224 is further operated under conditions to separate from the phenol and diethylene glycol rich and cyclohexanone lean stream in line 222 a diethylene glycol rich stream in line 228 as a bottoms that is richer in diethylene glycol than the phenol and diethylene glycol rich and cyclohexanone lean stream in line 222, for example, containing substantially all of the diethylene glycol and only 0.1 wt % of the phenol found in the phenol and diethylene glycol rich and cyclohexanone lean stream in line 222.

In one embodiment, during operation of the extractive distillation system 216 certain reactions take place that create components having a lower volatility and a reduced beneficial extractive effect relative to the solvent diethylene glycols, for example the enol-ethers described in WO2013/165659 that are a reaction product of cyclohexanone and diethylene glycol. It may be desirable to purge a portion of those and other low volatility components, and replace them with fresh diethylene glycol from outside the extractive distillation system to increase the efficiency of the circulating diethylene glycol in the extractive distillation system. Such an optional operation is represented by the bi-directional line 230. The circulating diethylene glycol solvent stream in line 232 may simply be the unadulterated entirety of the diethylene glycol rich stream in line 228. Alternatively, the circulating diethylene glycol solvent stream in line 232 may be a portion of the diethylene glycol rich stream in line 228, with another portion having been removed from it in line 230, e.g., to reduce the concentration of such lower volatility reactants within extractive distillation system 216. Further, the circulating diethylene glycol solvent stream in line 232 may be the entirety of the diethylene glycol rich stream in line 228 combined with a fresh diethylene glycol solvent stream in line 230, e.g., make-up solvent to replace diethylene glycol losses that may occur in the operation of extractive distillation system 216.

In an alternative embodiment not shown in FIG. 2, a second solid basic medium is employed. For example, the second combined product stream in line 212 may be directed to a solid basic medium in contacting device, such as described in FIG. 1, to form a treated combined product stream that is introduced to extraction column 218. As another example in this vein, an appropriate diethylene glycol containing stream within the extractive distillation system may be directed to a solid basic medium in a contacting device, conveniently the diethylene glycol rich stream in line 228.

Figure 3:
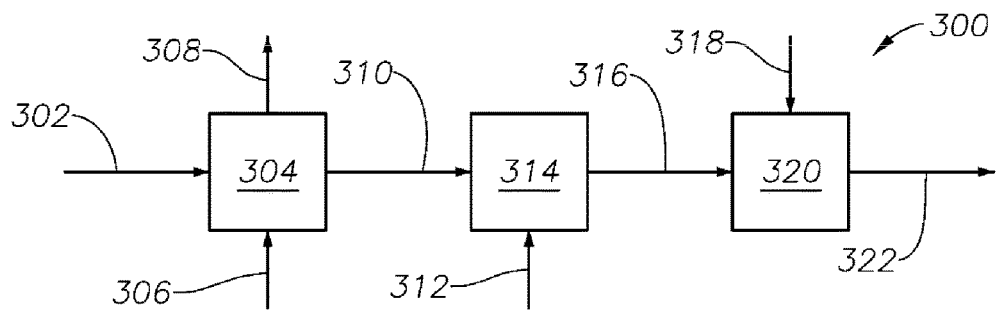
FIGS. 3 and 4 are schematic drawings showing comparative processes for making cyclohexanone and/or phenol.

FIG. 3 (Comparative Example)

Figure 4:
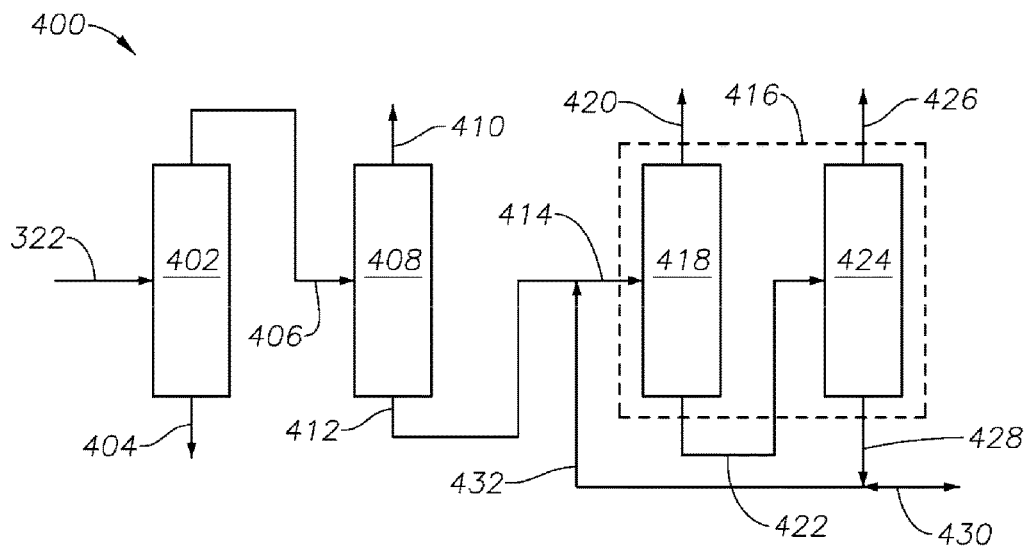

The example shown in this figure, in conjunction with the example of FIG. 4 that follows, demonstrates the hitherto unrecognized problem in the production of phenol and cyclohexanone via the cleavage of cyclohexylbenzene hydroperoxide with sulfuric acid when using a diamine to neutralize a cleavage product, and a diethylene glycol extractive distillation system to separate the derived phenol and cyclohexanone products. Such a cleavage product was produced in accordance with the following description of FIG. 3.

In a continuously operating system 300, a feedstock in line 302 comprising over 99.8 wt % cyclohexylbenzene and about 1000 wppm N-hydroxyphthalimide (NHPI) with a balance of bicyclohexane was provided to an oxidation reactor 304. A stream of air in line 306 as the source of oxygen was also provided to oxidation reactor 304. Conditions within oxidation reactor 304 were about 1 psig (6.89 kPa, gauge pressure) and 105° C., with vigorous mixing of the liquid and vapor such that an oxidation reaction occurred, causing cyclohexylbenzene hydroperoxide to form. An oxygen depleted air stream in line 308 was removed from oxidation reactor 304, along with an oxidation reaction product including about 25 wt % cyclohexyl-1-phenyl-1-hydroperoxide in line 310, and also including other hydroperoxides, water, and light contaminants hexanal and pentanoic acid, as well as NHPI, among other minor oxidized species.

The oxidation product in line 310 along with sulfuric acid line 312 was provided to cleavage reactor 314, such that the amount of sulfuric acid was about 500 wppm relative to the overall contents within cleavage reactor 314. Conditions in cleavage reactor 314 were about 40° C. and 5 psig (34.5 kPa, gauge pressure) such that a cleavage reaction took place, causing the cyclohexyl-1-phenyl-1-hydroperoxide to decompose to phenol and cyclohexanone and a contaminant byproduct. All other hydroperoxides were also converted, and a cleavage product including about 12.5 wt % phenol, 12.5 wt % cyclohexanone, unreacted cyclohexylbenzene and sulfuric acid and the aforementioned light contaminants and other byproduct contaminants were withdrawn from cleavage reactor 314 in line 316.

The cleavage product in line 316 and a 2-methylpentane-1,5-diamine in line 318 were directed to neutralization mixing device 320 such that the amount of diamine was about 1000 wppm relative to the combined streams in line 316 and 318. Conditions within neutralization mixing device 320 were such that a neutralization reaction occurred and an acid-diamine complex product was formed. A diamine neutralized cleavage product stream in line 322, having a higher pH relative to that of the cleavage product including sulfuric acid in line 316, was removed from neutralization mixing device 320.

FIG. 4 (Comparative Example)

This example, in conjunction with the example of FIG. 3 above, demonstrates the hitherto unrecognized problem in the production of phenol and cyclohexanone via the cleavage of cyclohexylbenzene hydroperoxide with sulfuric acid when using a diamine to neutralize a cleavage product, and a diethylene glycol extractive distillation system to separate the derived phenol and cyclohexanone products. In a continuously operating system 400 as shown in FIG. 4, attached to the section 300 of FIG. 3 discussed above, the 2-methylpentane-1,5-diamine neutralized cleavage product stream in line 322 was provided to a first distillation column 402. The general treatment of the diamine neutralized cleavage product stream in line 322 in FIG. 4 was similar to the description according to FIG. 2, except that the cleavage product stream in line 322 contains a great deal of sulfur having used a liquid diamine as a neutralizing agent rather than using a solid basic material per FIG. 2 that removed the sulfur instead of complexing it.

Referring to FIG. 4, the diamine neutralized cleavage product stream in line 322, having about 165 wppm sulfur, produced in accordance with Example 3 herein, was provided to a first distillation column 402. First distillation column 402 served to separate from the diamine neutralized cleavage product stream in line 322 a first bottoms product rich in cyclohexylbenzene and lean in phenol and components of higher volatility than phenol in line 404, and as an overhead product a first combined product stream rich in phenol and cyclohexanone and lean in cyclohexylbenzene and components of lower volatility than cyclohexylbenzene in line 406. The conditions within first distillation column 402 to which the diamine neutralized cleavage product stream in line 322 having about 165 wppm sulfur were exposed included a maximum temperature of at about 180° C. (in the reboiler).

The first combined product stream in line 406 further contains components of higher volatility than cyclohexanone as contaminants, e.g., hexanal, pentanoic acid and water. The first combined product stream in line 406 was directed to a second distillation column 408 that served to separate as a second overhead product a stream rich in those components of lower volatility and lean in phenol and cyclohexanone in line 410, and a second combined product stream as bottoms in line 412 that was richer in phenol and cyclohexanone than the first combined product stream. The amount of sulfur in the second combined product stream as bottoms in line 412 was measured, and found to have a quantity of sulfur of about 30 wppm.

Remaining with FIG. 4, the second combined product stream in line 412 was directed to an extractive distillation system within dashed line box 416, comprising an extraction column 418 and a solvent recovery column 424. The second combined product stream in line 412 was mixed with a circulating diethylene glycol solvent stream in line 432 to form a combined mixture and solvent stream in line 414 that was provided to extractive distillation column 418. Extraction column 418 was operated under conditions to separate from the combined mixture and solvent stream in line 414 a cyclohexanone rich stream in line 420 as an overhead product that was richer in cyclohexanone than the combined mixture and solvent stream in line 414, containing about 99.9 wt % of the cyclohexanone and only 0.01 wt % of the phenol found in the combined mixture and solvent stream, and no detectable diethylene glycol. Further, the cyclohexanone rich stream in line 420 contained from about 500 to almost 3000 wppm of 1,4-dixoane.

Extraction column 418 was further operated under conditions to separate from the second combined mixture and solvent stream in line 414 a phenol and diethylene glycol rich and cyclohexanone lean stream as a bottoms product in line 422 containing about 99.9 wt % of the phenol, and only 0.001 wt % of the cyclohexanone, and substantially all the diethylene glycol solvent found in the combined mixture and solvent stream in line 414. The bottoms temperature within extraction column 418 was about 160° C.

The phenol and diethylene glycol rich and cyclohexanone lean stream in line 422 was provided to solvent recovery column 424. Solvent recovery column 424 was operated under conditions to separate from the phenol and diethylene glycol rich and cyclohexanone lean stream in line 422 a phenol rich stream in line 426 as an overhead product that was richer in phenol than the phenol and diethylene glycol rich and cyclohexanone lean stream in line 422, containing 99.9 wt % of the phenol found in the phenol and diethylene glycol rich and cyclohexanone lean stream in line 422, and no detectable diethylene glycol. The phenol rich stream in line 426 was found to contain from about 500 to almost 3000 wppm of 1,4-dioxane.

Solvent recovery column 424 was further operated under conditions to separate from the phenol and diethylene glycol rich and cyclohexanone lean stream in line 422 a diethylene glycol rich stream in line 428 as a bottoms that was richer in diethylene glycol than the phenol and diethylene glycol rich and cyclohexanone lean stream in line 422, containing substantially all of the diethylene glycol and only 0.1 wt % of the phenol found in the phenol and diethylene glycol rich and cyclohexanone lean stream in line 422. In this particular operation described here in Example 4, no portion of the diethylene glycol rich stream in line 428 was taken as a purge in line 430, nor was any fresh diethylene glycol added in line 430, and the circulating diethylene glycol solvent stream in line 432 was the unadulterated entirety of the diethylene glycol rich stream in line 428.

Figure 5:
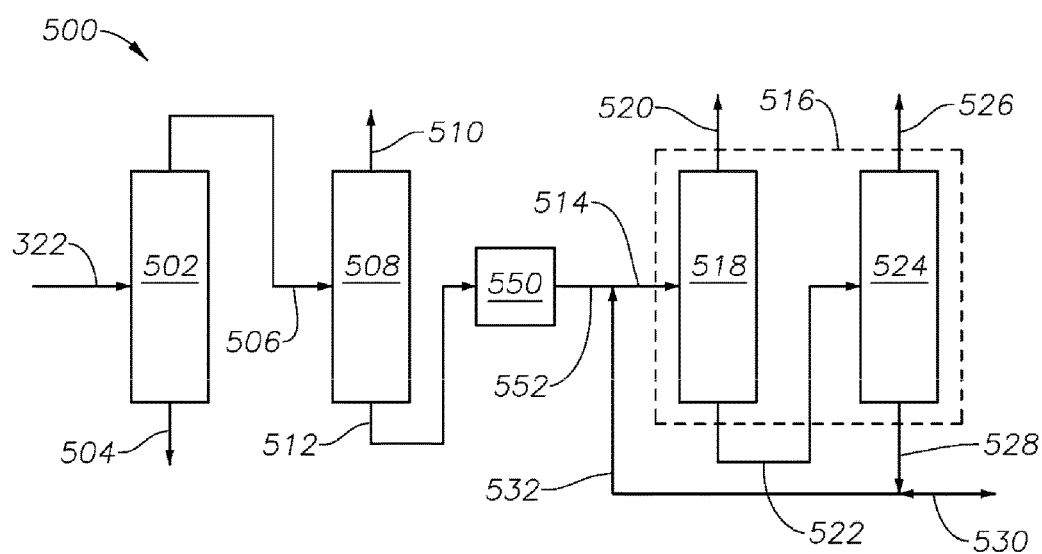
FIG. 5 is a schematic drawing showing an exemplary process of the present invention for making cyclohexanone and/or phenol.

FIG. 5 (Inventive Example)

This example demonstrates that removal of sulfur from the phenol and cyclohexanone derived from the cleavage product, and not simply complexation of the sulfur, can be used to make phenol and cyclohexanone products without the presence of 1,4-dioxane when using a diethylene glycol extractive distillation system. It stands in stark contrast to the results achieved in the example of FIG. 4.

In a continuously operating system 500 as shown in FIG. 5, attached to the section 300 of FIG. 3 discussed above, the 2-methylpentane-1,5-diamine neutralized cleavage product stream in line 322 was provided to a first distillation column 502. The general treatment of the diamine neutralized cleavage product stream in line 322 in FIG. 5 was similar to that of Example 4 and associated FIG. 4, except that the sulfur from the phenol and cyclohexanone derived from the diamine neutralized cleavage product was removed using a solid basic medium in treatment bed 550 prior to introduction to the extractive distillation system within dashed box 516.

Referring to FIG. 5, the diamine neutralized cleavage product stream in line 322, having about 165 wppm sulfur, produced in accordance with Example 3 herein, was provided to a first distillation column 502. First distillation column 502 served to separate from the diamine neutralized cleavage product stream in line 322 a first bottoms product rich in cyclohexylbenzene and lean in phenol and components of higher volatility than phenol in line 504, and as an overhead product a first combined product stream rich in phenol and cyclohexanone and lean in cyclohexylbenzene and components of lower volatility than cyclohexylbenzene in line 406. The conditions within first distillation column 502 to which the diamine neutralized cleavage product stream in line 322 having about 165 wppm sulfur were exposed included a maximum temperature of at about 180° C. (in the reboiler).

The first combined product stream in line 506 further contains components of higher volatility than cyclohexanone as contaminants, e.g., hexanal, pentanoic acid and water. The first combined product stream in line 506 was directed to a second distillation column 508 that served to separate as a second overhead product a stream rich in those components of lower volatility and lean in phenol and cyclohexanone in line 510, and a second combined product stream as bottoms in line 512 that was richer in phenol and cyclohexanone than the first combined product stream. The amount of sulfur in the second combined product stream as bottoms in line 512 was measured, and found to have a quantity of sulfur of about 30 wppm.

Remaining with FIG. 5, the second combined product stream in line 512 was directed to treatment bed 550. Within treatment bed 550 there was contained Amberlyst® A21 basic ion exchange resin pre-conditioned pursuant to manufacturer instructions for acid removal. The second combined product stream in line 512 was fed to treatment bed 550 at a rate of 75 grams per hour, and treatment bed 550 was operated at a temperature of about 25° C. and a pressure of about 15 psig (103 kPa, gauge pressure). The treated second combined product stream in line 552 was thus generated from treatment 550. The amount of sulfur in the treated second combined product stream as bottoms in line 552 was measured, and found to have no detectable sulfur.

The treated second combined product stream as bottoms in line 552 containing no detectable sulfur was provided to an extractive distillation system within dashed line box 516, comprising an extraction column 518 and a solvent recovery column 524. The treated second combined product stream in line 552 was mixed with a circulating diethylene glycol solvent stream in line 532 to form a combined mixture and solvent stream in line 514 that was provided to extractive distillation column 518. Extraction column 518 was operated under conditions to separate from the combined mixture and solvent stream in line 514 a cyclohexanone rich stream in line 520 as an overhead product that was richer in cyclohexanone than the combined mixture and solvent stream in line 514, containing about 99.9 wt % of the cyclohexanone and only 0.01 wt % of the phenol found in the combined mixture and solvent stream, and no detectable diethylene glycol. Further, the cyclohexanone rich stream in line 420 contained from no detectable (about 0) to about 5 wppm of 1,4-dixoane.

Extraction column 518 was further operated under conditions to separate from the second combined mixture and solvent stream in line 514 a phenol and diethylene glycol rich and cyclohexanone lean stream as a bottoms product in line 522 containing about 99.9 wt % of the phenol, and only 0.001 wt % of the cyclohexanone, and substantially all the diethylene glycol solvent found in the combined mixture and solvent stream in line 514. The bottoms temperature within extraction column 518 was about 160° C.

The phenol and diethylene glycol rich and cyclohexanone lean stream in line 522 was provided to solvent recovery column 524. Solvent recovery column 524 was operated under conditions to separate from the phenol and diethylene glycol rich and cyclohexanone lean stream in line 522 a phenol rich stream in line 526 as an overhead product that was richer in phenol than the phenol and diethylene glycol rich and cyclohexanone lean stream in line 522, containing 99.9 wt % of the phenol found in the phenol and diethylene glycol rich and cyclohexanone lean stream in line 522, and no detectable diethylene glycol. The phenol rich stream in line 426 was found to contain from no detectable (about 0) to about 5 wppm of 1,4-dixoane.

Solvent recovery column 524 was further operated under conditions to separate from the phenol and diethylene glycol rich and cyclohexanone lean stream in line 522 a diethylene glycol rich stream in line 528 as a bottoms that was richer in diethylene glycol than the phenol and diethylene glycol rich and cyclohexanone lean stream in line 522, containing substantially all of the diethylene glycol and only 0.1 wt % of the phenol found in the phenol and diethylene glycol rich and cyclohexanone lean stream in line 522. In this particular operation described here in Example 4, no portion of the diethylene glycol rich stream in line 528 was taken as a purge in line 530, nor was any fresh diethylene glycol added in line 530, and the circulating diethylene glycol solvent stream in line 532 was the unadulterated entirety of the diethylene glycol rich stream in line 528.

Figure 6:
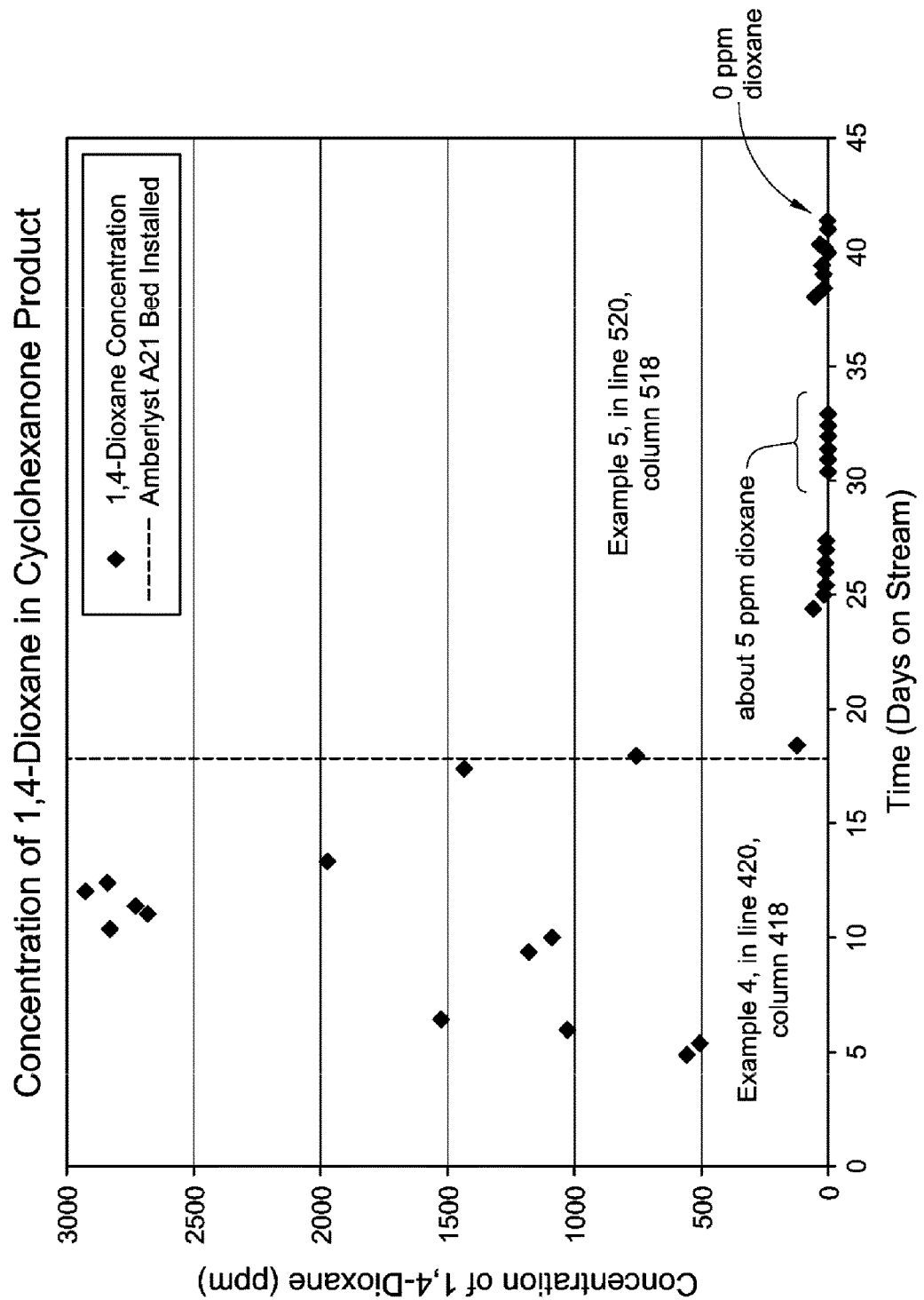
FIGS. 6 and 7 are diagrams showing concentrations of 1,4-dioxane in cyclohexanone and phenol products as a function of time in Example 5 herein.
Figure 7:
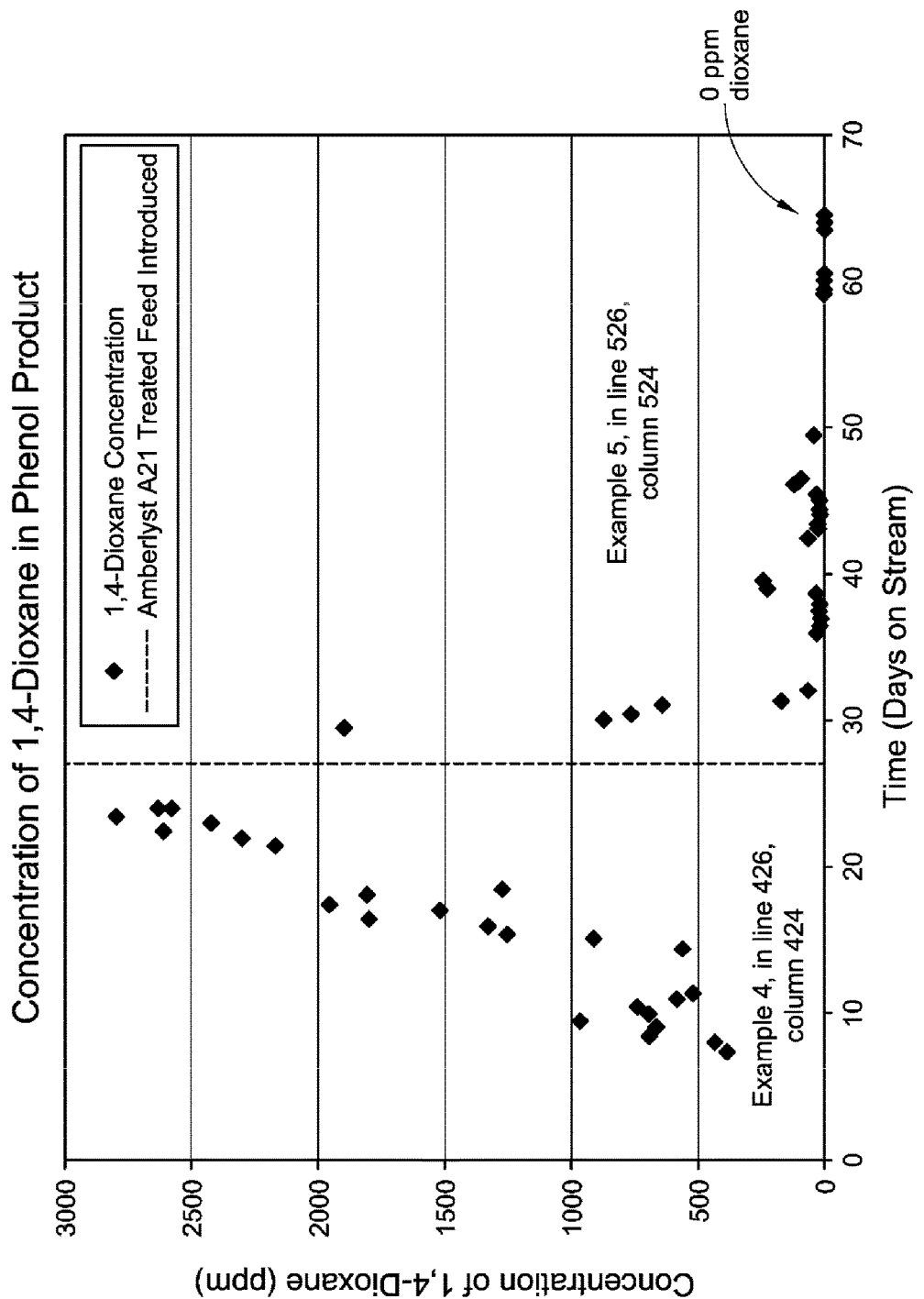

The amount of 1,4-dioxane in the cyclohexanone and phenol products generated in Examples 4 and 5 are shown graphically in FIGS. 6 and 7, respectively. The drastic reduction in 1,4-dioxane concentrations in phenol and cyclohexanone products after removal of sulfur from the distillation feeds derived from the cleavage product is evident. Removing the sulfur from the feed to the distillation column using a solid basic medium, as opposed to simply complexation of the sulfur using a liquid amine and then sending the complexation product along with the feeds to the distillation column as disclosed in the prior art, is particularly helpful in making phenol and cyclohexanone products without the presence of 1,4-dioxane when using a diethylene glycol extractive distillation system.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The present invention includes the following non-limiting embodiments.

A1. A process for separating a first mixture comprising cyclohexanone, phenol, cyclohexylbenzene, and a sulfur-containing component, comprising the following steps:

(A-I) contacting the first mixture with a pre-distillation solid-phase basic material to produce a second mixture comprising the sulfur-containing component at a concentration lower than in the first mixture;

(A-II) supplying the second mixture into a first distillation column operating at a temperature of at least 120° C.; and (A-III) obtaining an upper effluent and a lower effluent from the first distillation column, wherein the upper effluent has a higher concentration in cyclohexanone than the lower effluent, and the lower effluent has a higher cyclohexylbenzene concentration than the upper effluent.

A2. The process of A1, wherein the first mixture comprises sulfur at a total concentration in a range from 80 ppm to 2000 ppm by weight, based on the total weight of the first mixture.

A3. The process of A1 or A2, wherein the sulfur-containing component is sulfuric acid, and the first mixture comprises sulfuric acid at a concentration in a range from 80 ppm to 2000 ppm by weight, based on the total weight of the first mixture.

A4. The process of any of A1 to A3, wherein the second mixture comprises sulfur at a total concentration no greater than 10 ppm by weight, based on the total weight of the second mixture.

A5. The process of any of A1 to A4, wherein the second mixture comprises sulfuric acid at a concentration no greater than 10 ppm by weight, based on the total weight of the second mixture.

A6. The process of any of A1 to A5, wherein the upper effluent comprises sulfur at a total concentration no greater than 10 ppm by weight, based on the total weight of the upper effluent.

A7. The process of any of A1 to A6, wherein the upper effluent comprises sulfuric acid at a concentration no greater than 10 ppm by weight, based on the total weight of the upper effluent.

A8. The process of any of A1 to A7, wherein the first distillation column operates at a temperature of at least 150° C.

A9. The process of any of A1 to A8, wherein the first distillation column operates at a temperature of at least 170° C.

A10. The process of any of A1 to A9, wherein the first distillation column operates at a temperature higher than the disassociation temperature of at least one of the complexes between sulfuric acid and the following amines: (i) pentane-1,5-diamine; (ii) 1-methylhexane-1,5-diamine; (iii) hexane-1,6-diamine; (iv) 2-methylpentane-1,5-diamine; (v) ethylene diamine; (vi) propylene diamine; (vii) diethylene triamine; and (viii) triethylene tetramine.

A11. The process of any of A1 to A10, wherein the pre-distillation solid-phase basic material is selected from: (i) oxides of alkali metals alkaline earth metals, and zinc; (ii) hydroxides of alkali metals alkaline earth metals, and zinc; (iii) carbonates of alkali metals alkaline earth metals, and zinc; (iv) bicarbonates of alkali metals alkaline earth metals, and zinc; (v) complexes of two or more of (i), (ii), (iii), and (iv); (vi) solid amines; (vii) ion-exchange resins; and (viii) mixtures and combinations thereof.

A12. The process of A11, wherein the pre-distillation solid-phase basic material comprises an ion-exchange resin selected from strong base anion resins and weak base anion resins.

A13. The process of any of A1 to A12, wherein the upper effluent comprises cyclohexanone and phenol, and the process further comprises:

(A-IV) supplying at least a portion of the upper effluent and an extractive distillation solvent into an extractive distillation column;

(A-V) obtaining an upper cyclohexanone effluent and a lower extraction effluent from the extractive distillation column wherein the upper cyclohexanone effluent comprises cyclohexanone at a concentration of at least 90 wt %, and the lower extraction effluent comprises phenol and the extractive distillation solvent;

(A-VI) supplying at least a portion of the lower extraction effluent to a solvent distillation column; and (A-VII) obtaining an upper phenol effluent and a lower solvent effluent from the solvent distillation column.

A14. The process of A13, wherein the extractive distillation solvent is selected from: sulfolane; diols; cyclic ethers; and mixtures and combinations thereof.

A15. The process of A14, wherein the extractive distillation solvent comprises a glycol, and at least one of the upper cyclohexanone effluent and the upper phenol effluent has a total concentration of cyclic ethers produced from condensation reaction(s) of the glycol of no more than 10 ppm by weight, based on the total weight of the respective upper cyclohexanone effluent or the upper phenol effluent.

A16. The process of A15, wherein the extractive distillation solvent comprises diethylene glycol, and at least one of the upper cyclohexanone effluent and the upper phenol effluent has a concentration of 1,4-dioxane of no more than 10 ppm by weight, based on the total weight of the respective upper cyclohexanone effluent or the upper phenol effluent.

A17. The process of any of A13 to A16, wherein in step (A-IV), the portion of the upper effluent is obtained by contacting a part of the upper effluent with a pre-extraction solid-phase basic material, the same as or different from the pre-distillation solid-phase basic material.

A18. The process of any of A13 to A17, wherein in the liquid medium inside the extractive distillation column, the total concentration of sulfuric acid is at most 10 ppm by weight, based on the total weight of the liquid medium.

A19. The process of A18, wherein the liquid medium inside the extractive distillation column, the concentration of sulfur is at most 10 ppm by weight, based on the total weight of the liquid medium.

A20. The process of any of A1 to A19, wherein the first mixture is produced by:

(A-I-1) supplying a cleavage feed comprising cyclohexyl-1-phenyl-1-hydroperoxide and cyclohexylbenzene into a cleavage reactor; and (A-I-2) cleaving at least a portion of the cyclohexyl-1-phenyl-1-hydroperoxide in a medium comprising sulfuric acid in the cleavage reactor.

B1. A process for making phenol and/or cyclohexanone from an extraction distillation feed comprising phenol and cyclohexanone, comprising the following steps:

(B-i) controlling the concentration of an acid in the extraction distillation feed at a level no greater than 10 ppm by weight, based on the total weight of the extraction distillation feed;

(B-ii) supplying at least a portion of the extraction distillation feed and an extractive distillation solvent into an extractive distillation column;

(B-iii) obtaining an upper cyclohexanone effluent and a lower extraction effluent from the extractive distillation column wherein the upper cyclohexanone effluent comprises cyclohexanone at a concentration of at least 90 wt %, and the lower extraction effluent comprises phenol and the extractive distillation solvent;

(B-iv) supplying at least a portion of the lower extraction effluent to a solvent distillation column; and (B-v) obtaining an upper phenol effluent and a lower solvent effluent from the solvent distillation column.

B2. The process of B1, wherein the extractive distillation solvent is selected from: sulfolane; diols; cyclic ethers; and mixtures and combinations thereof.

B3. The process of B2, wherein the extractive distillation solvent comprises a glycol, and at least one of the upper cyclohexanone effluent and the upper phenol effluent has a total concentration of cyclic ethers produced from condensation reaction(s) of the glycol of no more than 10 ppm by weight, based on the total weight of the respective upper cyclohexanone effluent or the upper phenol effluent.

B4. The process of B3, wherein the extractive distillation solvent comprises diethylene glycol, and at least one of the upper cyclohexanone effluent and the upper phenol effluent has a concentration of 1,4-dioxane of no more than 10 ppm by weight, based on the total weight of the respective upper cyclohexanone effluent or the upper phenol effluent.

B5. The process of any of B1 to B4, wherein step (B-i) comprises contacting at least a portion of the extraction distillation feed with a pre-extraction solid-phase basic material.

B6. The process of any of B1 to B5, wherein in the liquid medium inside the extractive distillation column, the total concentration of sulfuric acid is at most 10 ppm by weight, based on the total weight of the liquid medium.

B7. The process of B6, wherein in the liquid medium inside the extractive distillation column, the concentration of sulfur is at most 10 ppm by weight, based on the total weight of the liquid medium.

B8. The process of any of B1 to B7, wherein the pre-extraction solid-phase basic material is selected from: (i) oxides of alkali metals alkaline earth metals, and zinc; (ii) hydroxides of alkali metals alkaline earth metals, and zinc; (iii) carbonates of alkali metals alkaline earth metals, and zinc; (iv) bicarbonates of alkali metals alkaline earth metals, and zinc; (v) complexes of two or more of (i), (ii), (iii), and (iv); (vi) solid amines; (vii) ion-exchange resins; and (viii) mixtures and combinations thereof.

B9. The process of B8, wherein the pre-extraction solid-phase basic material comprises an ion-exchange resin.

B10. The process of any of B1 to B9, wherein step (B-i) comprises:

(B-i-1) providing a first mixture comprising cyclohexanone, phenol, cyclohexylbenzene, and sulfuric acid;

(B-i-2) contacting the first mixture with a pre-distillation solid-phase basic material to produce a second mixture comprising sulfuric acid at a concentration lower than in the first mixture;

(B-i-3) supplying the second mixture into a distillation column operating at a temperature of at least 120° C.;

(B-i-4) obtaining an upper effluent and a lower effluent from the first distillation column, wherein the upper effluent has a higher concentration in cyclohexanone than the lower effluent, and the lower effluent has a higher cyclohexylbenzene concentration than the upper effluent; and (B-i-5) supplying at least a portion of the upper effluent as the extraction distillation feed.

B11. The process of B10, wherein the first mixture comprises sulfur at a total concentration in a range from 80 ppm to 2000 ppm by weight, based on the total weight of the first mixture.

B12. The process of B10 or B11, wherein the first mixture comprises sulfuric acid at a concentration in a range from 80 ppm to 2000 ppm by weight, based on the total weight of the first mixture.

B13. The process of any of B10 to B12, wherein the second mixture comprises sulfur at a total concentration no greater than 10 ppm by weight, based on the total weight of the second mixture.

B14. The process of any of B10 to B13, wherein the second mixture comprises sulfuric acid at a concentration no greater than 10 ppm by weight, based on the total weight of the second mixture.

B15. The process of any of B10 to B14, wherein the upper effluent comprises sulfur at a total concentration no greater than 10 ppm by weight, based on the total weight of the upper effluent.

B16. The process of any of B10 to B15, wherein the upper effluent comprises sulfuric acid at a concentration no greater than 10 ppm by weight, based on the total weight of the upper effluent.

B17. The process of any of B10 to B16, wherein the first distillation column operates at a temperature of at least 150° C.

B18. The process of any of B10 to B17, wherein the first distillation column operates at a temperature of at least 170° C.

B19. The process of any of B10 to B18, wherein the first distillation column operates at a temperature higher than the disassociation temperature of at least one of the complexes between sulfuric acid and the following amines: (i) pentane-1,5-diamine; (ii) 1-methylhexane-1,5-diamine; (iii) hexane-1,6-diamine; (iv) 2-methylpentane-1,5-diamine; (v) ethylene diamine; (vi) propylene diamine; (vii) diethylene triamine; and (viii) triethylene tetramine.

B20. The process of any of B10 to B19, wherein the first mixture is produced by:
(B-i-1-a) supplying a cleavage feed comprising cyclohexyl-1-phenyl-1-hydroperoxide and cyclohexylbenzene into a cleavage reactor; and
(B-i-1-b) cleaving at least a portion of the cyclohexyl-1-phenyl-1-hydroperoxide in a medium comprising sulfuric acid in the cleavage reactor.

The invention claimed is:

1. A process for separating a first mixture comprising cyclohexanone, phenol, cyclohexylbenzene, and a sulfuric acid, comprising the following steps:
(I) contacting the first mixture with a pre-distillation solid-phase basic material to produce a second mixture comprising the sulfuric acid at a concentration lower than in the first mixture;
(II) supplying the second mixture into a distillation column operating at a temperature of at least 120° C. and no higher than the decomposition temperature of the sulfuric acid;
(III) obtaining an upper effluent and a lower effluent from the first distillation column, wherein the upper effluent has a higher concentration in cyclohexanone than the lower effluent, and the lower effluent has a higher cyclohexylbenzene concentration than the upper effluent;
(IV) supplying at least a portion of the upper effluent and an extractive distillation solvent into an extractive distillation column, wherein portion of the upper effluent is obtained by contacting a part of the upper effluent with a pre-extraction solid-phase basic material which is the same as or different from the pre-distillation solid-phase basic material;
(V) obtaining an upper cyclohexanone effluent and a lower extraction effluent from the extractive distillation column wherein the upper cyclohexanone effluent comprises cyclohexanone at a concentration of at least 90 wt %, and the lower extraction effluent comprises phenol and the extractive distillation solvent;
(VI) supplying at least a portion of the lower extraction effluent to a solvent distillation column; and
(VII) obtaining an upper phenol effluent and a lower solvent effluent from the solvent distillation column.

2. The process of claim 1, wherein at least one of the following conditions is met:
(i) the first mixture comprises sulfur at a total concentration in a range from 80 ppm to 2000 ppm by weight, based on the total weight of the first mixture; and
(ii) the first mixture comprises sulfuric acid at a concentration in a range from 80 ppm to 2000 ppm by weight, based on the total weight of the first mixture.

3. The process of claim 1, wherein at least one of the following conditions is met:
(i) the second mixture comprises sulfur at a total concentration no greater than 10 ppm by weight, based on the total weight of the second mixture; and
(ii) the second mixture comprises sulfuric acid at a concentration no greater than 10 ppm by weight, based on the total weight of the second mixture.

4. The process of claim 1, wherein at least one of the following conditions is met:
(i) the upper effluent comprises sulfur at a total concentration no greater than 10 ppm by weight, based on the total weight of the upper effluent; and
(ii) the upper effluent comprises sulfuric acid at a concentration no greater than 10 ppm by weight, based on the total weight of the upper effluent.

5. The process of claim 1, wherein the first distillation column operates at a temperature of at least 150° C.

6. The process of claim 1, wherein the first distillation column operates at a temperature higher than the disassociation temperature of at least one of the following: (i) pentane-1,5-diamine sulfuric acid complex; (ii) 1-methylhexane-1,5-diamine sulfuric acid complex; (iii) 2-methylpentane-1,5-diamine sulfuric acid complex; and (iv) hexane-1,6-diamine sulfuric acid complex.

7. The process of claim 1, wherein the pre-distillation solid-phase basic material is selected from: (i) oxides of alkali metals alkaline earth metals, and zinc; (ii) hydroxides of alkali metals alkaline earth metals, and zinc; (iii) carbonates of alkali metals alkaline earth metals, and zinc; (iv) bicarbonates of alkali metals alkaline earth metals, and zinc; (v) complexes of two or more of (i), (ii), (iii), and (iv); (vi) solid amines; (vii) ion-exchange resins; and (viii) mixtures and combinations thereof.

8. The process of claim 7, wherein the pre-distillation solid-phase basic material comprises an ion-exchange resin.

9. The process of claim 8, wherein the extractive distillation solvent comprises a glycol, and at least one of the upper cyclohexanone effluent and the upper phenol effluent has a total concentration of cyclic ethers produced from condensation reaction(s) of the glycol of no more than 10 ppm by weight, based on the total weight of the respective upper cyclohexanone effluent or the upper phenol effluent.

10. The process of claim 9, wherein the extractive distillation solvent comprises diethylene glycol, and at least one of the upper cyclohexanone effluent and the upper phenol effluent has a concentration of 1,4-dioxane of no more than 10 ppm by weight, based on the total weight of the respective upper cyclohexanone effluent or the upper phenol effluent.

11. The process of claim 8, wherein in the liquid medium inside the extractive distillation column, at least one of the following conditions is met:
   (i) the total concentration of sulfuric acid is at most 10 ppm by weight, based on the total weight of the liquid medium; and
   (ii) the total concentration of sulfur is at most 10 ppm by weight, based on the total weight of the liquid medium.

12. A process for making phenol and/or cyclohexanone from an extraction distillation feed comprising phenol and cyclohexanone, comprising the following steps:
   (i) controlling the concentration of an acid in the extraction distillation feed at a level no greater than 10 ppm by weight, based on the total weight of the extraction distillation feed, by contacting at least a portion of the extraction distillation feed with a pre-extraction solid-phase basic material;
   (ii) supplying at least a portion of the extraction distillation feed and an extractive distillation solvent into an extractive distillation column;
   (iii) obtaining an upper cyclohexanone effluent and a lower extraction effluent from the extractive distillation column, wherein the upper cyclohexanone effluent comprises cyclohexanone at a concentration of at least 90 wt %, and the lower extraction effluent comprises phenol and the extractive distillation solvent;
   (iv) supplying at least a portion of the lower extraction effluent to a solvent distillation column; and
   (v) obtaining an upper phenol effluent and a lower solvent effluent from the solvent distillation column.

13. The process of claim 12, wherein the extractive distillation solvent comprises a glycol, and at least one of the upper cyclohexanone effluent and the upper phenol effluent has a total concentration of cyclic ethers produced from condensation reaction(s) of the glycol of no more than 10 ppm by weight, based on the total weight of the respective upper cyclohexanone effluent or the upper phenol effluent.

14. The process of claim 13, wherein the extractive distillation solvent comprises diethylene glycol, and at least one of the upper cyclohexanone effluent and the upper phenol effluent has a concentration of 1,4-dioxane of no more than 10 ppm by weight, based on the total weight of the respective upper cyclohexanone effluent or the upper phenol effluent.

15. The process of claim 12, wherein in the liquid medium inside the extractive distillation column, at least one of the following conditions is met:
   (i) the total concentration of sulfuric acid is at most 10 ppm by weight, based on the total weight of the liquid medium; and
   (ii) the total concentration of sulfur is at most 10 ppm by weight, based on the total weight of the liquid medium.

16. The process of claim 12, wherein the pre-extraction solid-phase basic material is selected from: (i) oxides of alkali metals alkaline earth metals, and zinc; (ii) hydroxides of alkali metals alkaline earth metals, and zinc; (iii) carbonates of alkali metals alkaline earth metals, and zinc; (iv) bicarbonates of alkali metals alkaline earth metals, and zinc; (v) complexes of two or more of (i), (ii), (iii), and (iv); (vi) solid amines; (vii) ion-exchange resins; and (viii) mixtures and combinations thereof.

17. The process of claim 16, wherein the pre-extraction solid-phase basic material comprises an ion-exchange resin.

18. The process of claim 12, wherein step (i) comprises:
   (i-1) providing a first mixture comprising cyclohexanone, phenol, cyclohexylbenzene, and sulfuric acid;
   (i-2) contacting the first mixture with a pre-distillation solid-phase basic material to produce a second mixture comprising sulfuric acid at a concentration lower than in the first mixture;
   (i-3) supplying the second mixture into a distillation column operating at a temperature of at least 120° C.;
   (i-4) obtaining an upper effluent and a lower effluent from the first distillation column, wherein the upper effluent has a higher concentration in cyclohexanone than the lower effluent, and the lower effluent has a higher cyclohexylbenzene concentration than the upper effluent; and
   (i-5) supplying at least a portion of the upper effluent as the extraction distillation feed.

19. The process of claim 18, wherein at least one of the following conditions is met:
   (i) the first mixture comprises sulfur at a total concentration in a range from 80 ppm to 2000 ppm by weight, based on the total weight of the first mixture; and
   (ii) the first mixture comprises sulfuric acid at a concentration in a range from 80 ppm to 2000 ppm by weight, based on the total weight of the first mixture.

20. The process of claim 18, wherein at least one of the following conditions is met:
   (i) the second mixture comprises sulfur at a total concentration no greater than 10 ppm by weight, based on the total weight of the second mixture; and
   (ii) the second mixture comprises sulfuric acid at a concentration no greater than 10 ppm by weight, based on the total weight of the second mixture.

21. The process of claim 18, wherein at least one of the following conditions is met:
   (i) the upper effluent comprises sulfur at a total concentration no greater than 10 ppm by weight, based on the total weight of the upper effluent; and
   (ii) the upper effluent comprises sulfuric acid at a concentration no greater than 10 ppm by weight, based on the total weight of the upper effluent.

22. The process of claim 18, wherein the first distillation column operates at a temperature of at least 150° C.

* * * * *